United States Patent [19]

Ito et al.

[11] 4,166,697
[45] Sep. 4, 1979

[54] SPECTROPHOTOMETER EMPLOYING MAGNETO-OPTIC EFFECT

[75] Inventors: Masaru Ito, Kodaira; Seiichi Murayama, Kokubunji; Manabu Yamamoto, Odawara; Kounosuke Ohishi, Mito, all of Japan

[73] Assignee: Hitachi, Ltd., Japan

[21] Appl. No.: 836,971

[22] Filed: Sep. 27, 1977

[30] Foreign Application Priority Data

Oct. 1, 1976 [JP] Japan .................. 51-117161

[51] Int. Cl.² .............................................. G01J 3/42
[52] U.S. Cl. .................................... 356/319; 356/312
[58] Field of Search .................................. 356/85–88, 356/93–97

[56] References Cited

U.S. PATENT DOCUMENTS 4,035,083  7/1977  Woodriff et al. .................. 356/82

FOREIGN PATENT DOCUMENTS 2165106  7/1972  Fed. Rep. of Germany .............. 356/87

OTHER PUBLICATIONS

Uchida et al., *Oyo Buturi*, vol. 44, No. 8, Aug. 1975, pp. 852 (16)–857 (21).

*Primary Examiner*—F. L. Evans
*Attorney, Agent, or Firm*—Craig and Antonelli

[57] ABSTRACT

This application discloses a spectrophotometer employing a magneto-optic effect which enables quantitative analysis of a sample to be measured by a double beam method. In performing the double beam method for analyzing the sample, a magnetic field is applied to the sample along with linearly polarized light from a light source, the forward scattered light scattered by the sample atoms and the incident linearly polarized light from the sample are converted into two cross-polarized beams of light using an analyzer, and these two beams of cross-polarized light are spectrally analyzed by a single dispersive element. The spectrophotometer of the invention provides an arrangement such that the plane defined by the above-mentioned two beams of light is perpendicular to the plane of dispersion of the dispersive element, and the two beams of light so dispersed are independently detected by separate detectors.

6 Claims, 9 Drawing Figures

SPECTROPHOTOMETER EMPLOYING MAGNETO-OPTIC EFFECT

FIELD OF THE INVENTION

The present invention relates to a spectrophotometer employing the magneto-optic effect to compensate for the effects of errors due to light source fluctuation and light absorption by the sample.

PRIOR ART OF THE INVENTION

When light enters a space in which atoms are randomly distributed and is scattered by the atoms, the mode of scattering of the light is twofold; one causing a change in the wavelength of the light before and after scattering, and the other causing no change in the wavelength. In the case of the latter, the intensity of the light scattered in the same direction as the incoming direction of the incident light, i.e., the intensity of the forward scattered light, if the intensity of the light is so low that the absorption of the light by the atoms in the space is negligible, is proportional to the square of the number of the atoms involved in the scattering. Additionally, the intensity of the light scattered in directions other than that of the forward scattered light is proportional to the number of the atoms involved in the scattering.

On the other hand, in the case of resonance scattering in which the wavelength of the incident light coincides with that of the resonance line of the atoms, the intensity of the scattered light remarkably increases when compared with non-resonance scattering. The wavelength of the resonance line varies from element to element and is well known. Accordingly, a sample atom for measurement can be analyzed at a high sensitivity when light having the same resonance line as that of the sample atom is allowed to enter a space containing the sample atom and the forward scattered light due to the atoms is then measured.

In the case of the forward scattered light, however, the wavelength and the travelling direction of the incident light are the same as those of the scattered light. It is therefore absolutely necessary to somehow distinguish between the incident light and the scattered light.

According to the article of A. Corney, B. P. Kibble and G. W. Series ["Proceedings of the Royal Society of London", Vol. A293, page 70 (1966)], when a magnetic field is applied to atoms, the polarization of the scattered light becomes different than that of the incident light due to the Faraday effect or Voigt effect, and the forward scattered light is observed more intensely than other scattered light also in the case of a magneto-optic effect. D. A. Church and T. H. Hadeishi state in "Applied Physics Letters", Vol. 24, page 185 (1974) that the above-mentioned fact disclosed by Corney et al can be adapted to the analysis of a sample atom for measurement.

Figure 1:
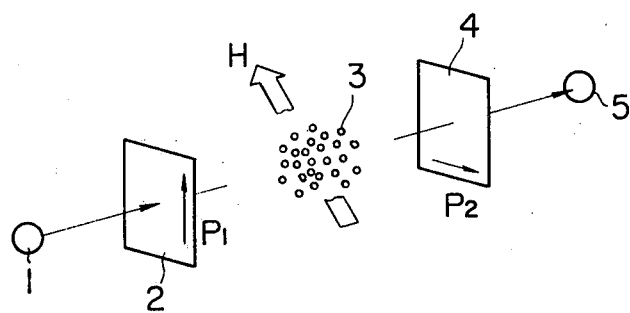
FIG. 1 is a schematic view showing the principle of analytical measurement of a trace element using a magneto-optic effect.

Namely, the principle of measurement is schematically illustrated in FIG. 1. A ray of light from a light source 1 emitting a spectrum having the same wavelength as that of the resonance line of an atom to be measured is converted via a polarizer 2 into linearly polarized light having a polarization direction $P_1$ and allowed to enter a space including the sample atoms 3 for measurement. The incident linearly polarized light is scattered by the sample atoms (usually in the vapor state). When a magnetic field H is applied to the sample space in parallel with (or perpendicular to) the direction of advance of the incident linearly polarized light, the polarization of the scattered light is varied from that of the incident light due to the Faraday effect or Voigt effect.

The incident light and the forward scattered light are caused to enter an analyzer 4 whereby only the forward scattered light component having a polarization plane $P_2$ crossing at right angles the polarization direction $P_1$ of the incident linearly polarized light is allowed to pass through the analyzer 4 and detected by a detector 5. By the use of a double image polarization prism as the analyzer 4, it is possible to simultaneously detect two polarization components crossing at right angles to each other, i.e., the incident linearly polarized light and the forward scattered light. The mode of scattering and detection is illustrated in FIGS. 2a and 2b.

Figure 2A:
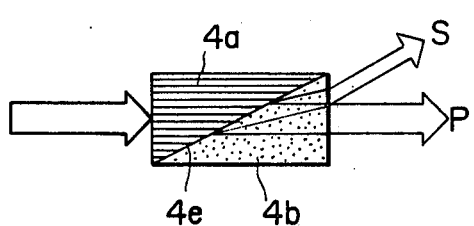
FIGS. 2a and 2b are schematic views each showing the state of polarization in the magneto-optic spectrophotometer in accordance with the kind of a double-image polarization prism used.
Figure 2B:
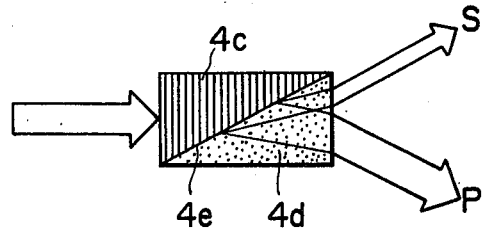

A Rochon prism is shown used as the analyzer in FIG. 2a and a Wollaston prism as the analyzer in FIG. 2b. Each prism consists of two kinds of optically uniaxial, anisotropic crystals bonded to each other with their optic axis being deviated by 90 degrees. The Rochon prism of FIG. 2a consists of a rectangular prism 4a having its optic axis in parallel with the travelling direction of the incident light and a rectangular prism 4b having its optic axis in parallel with an inclined plane 4e of the prism 4a perpendicular to the travelling direction of the incident light, and bonded to the former prism 4a. When the light is incident upon the prism as indicated by an arrow, the transmitted light from the Rochon prism is divided into two mutually perpendicular polarized light beams having different directions of transmission. Among these two separated rays of light polarized with respect to the inclined plane 4e, i.e., the interface between two rectangular prism 4a and 4b, one separated ray P, comprising light polarized in the direction of the incident plane 4e (into the plane of the drawing), advances without being refracted while the other separated light ray S, which is perpendicularly polarized into the incident plane, is refracted as it advances.

In the Wollaston prism shown in FIG. 2b, the optic axis of the prism 4c on the incident side is located in the incident plane relative to the inclined plane 4e and perpendicular to the incident light. Hence, both of the transmitted rays P and S are refracted. As illustrated in these examples, the direction of the two rays P and S separated by the double image polarization prism is determined by the direction of the inclined surface 4e.

Figure 3:
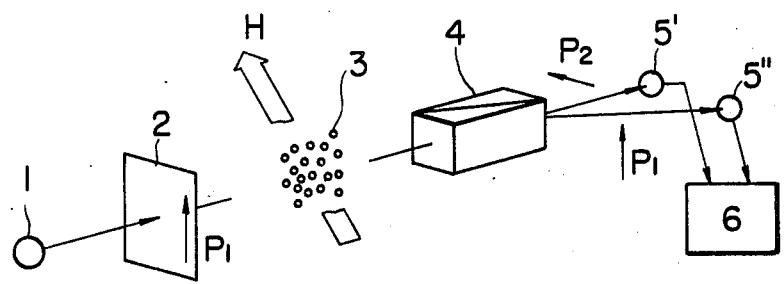
FIG. 3 is a schematic view showing the principle of measurement of a sample by a double beam method in the magneto-optic spectrophotometer.

FIG. 3 shows a method of measurement in accordance with a double beam method for correcting the measurement error arising from the fluctuation in the intensity of the incident light or the light absorption of molecules. In this FIG. 3, reference numeral 1 represents a light source which emits light including the resonance line of a sample atom to be measured, and 2 denotes a polarizer. The symbol H designates a magnetic field applied to the atoms in a direction perpendicular to the incident light (which may be applied in a direction parallel to the incident light). The numeral 3 denotes atoms; 4 an analyzer (double image prism); 5' and 5" detectors; and 6 an operational apparatus.

The measuring system shown is arranged such that when the atoms 3 for measurement are absent, only one ray of light is allowed to pass through the analyzer 4 of the double image polarization prism. In this instance, the light transmitted through the analyzer 4 has the same polarization plane $P_1$ as that of the incident linear polarization and is detected by the detector 5". If the atoms 3 to be detected are present, two rays of light pass through the analyzer 4. The light newly appearing in this instance has a polarization plane $P_2$ which is perpendicular to light ray $P_1$, and is detected by the detector 5'. Since the light having both polarization planes $P_1$ and $P_2$ is subject to absorption and scattering in the same proportion by molecules nd particles, the measurement error due to the fluctuation in the intensity of the incident light or to the absorption of the molecules can be compensated for by proportioning the output of the detector 5' and that of the detector 5" using the operational apparatus 6. It is also possible to analyze various elements by interposing a wavelength selector between the detectors 5' and 5" and the analyser 4 so as to select a desired wavelength.

The inventors of this invention previously filed a Japanese Patent Application No. 143979/1975 entitled "MAGNETO-OPTIC SPECTROPHOTOMETER" (U.S. patent application Ser. No. 746,831) and disclosed that the elementary analysis of a given sample can be made in a highly accurate manner by first separating light coming out from a sample chamber which has been subjected to a magnetic field into an ordinary ray and an extraordinary ray. This separation is performed by the use of a double image polarization prism. Then both light rays are converged into the same entrance slit of the same spectrophotometer and separated by using a single dispersive element. Finally, these light rays are separately detected by separate detectors and a comparative measured value of the intensity of polarized light is obtained using the other light (incident light) as a reference.

Figure 4:
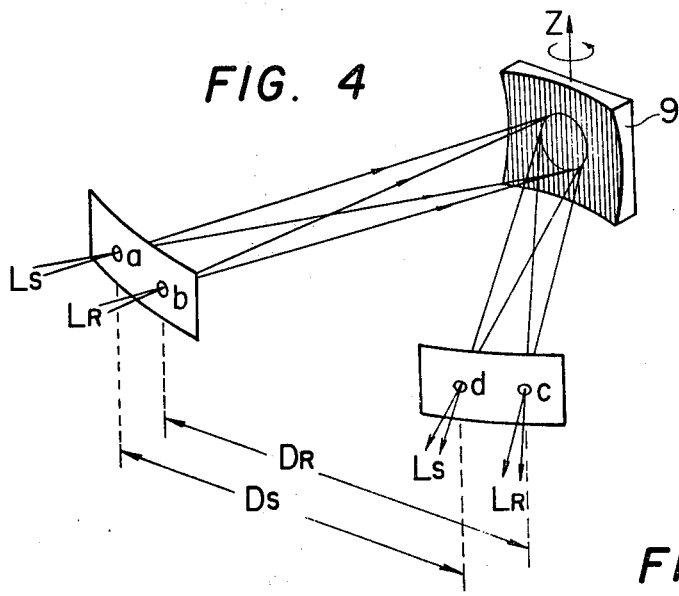
FIG. 4 is a schematic view showing the relation between incident light and diffracted light when two beams of light of the same wavelength are allowed to enter a concave diffraction grating with mutually different angles of incidence, the plane including these beams being at right angles to the grooves of the grating.
Figure 5:
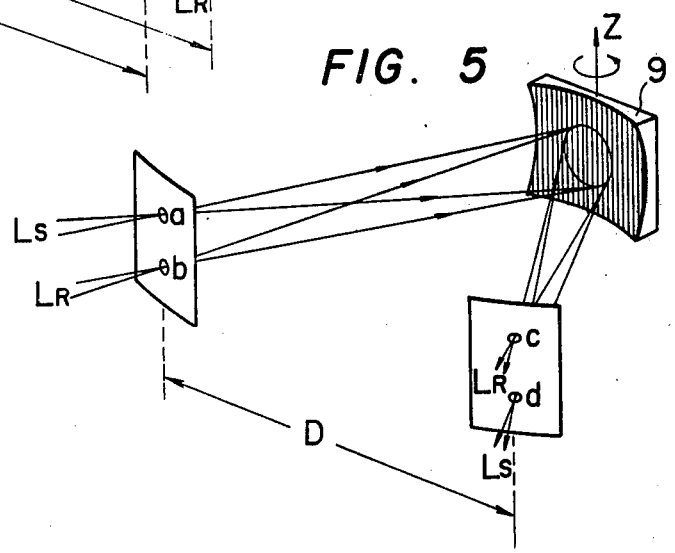
FIG. 5 is a schematic view showing the principal section of the apparatus in accordance with an embodiment of the present invention.

However, there are two cases as shown in FIGS. 4 and 5 where two light beams $L_S$ and $L_R$ having the same wavelength but different travelling directions enter a dispersive element. To simplify the explanation, a concave diffraction grating is shown as the dispersive element in these drawings, though the explanation also applies to a plane diffraction grating or a prism.

FIG. 4 shows the case where the optical axes of two light rays having the same wavelength but different travelling directions lie in a plane perpendicular to the plane including the direction of the grooves of the diffraction grating 9, that is, in the plane consisting of the dispersion direction. The two light beams $L_S$, $L_R$ entering through the entrance pin-holes a, b of the entrance plate 7 are diffracted by the diffraction grating 9, respectively, and form images between exit pin-holes d and c on the exit plate 8. When the distances between the pin-holes a and d and between b and c are designated $D_S$ and $D_R$, respectively, $D_S$ and $D_R$ vary in accordance with the wavelength. Hence, it is necessary to change the distance between c and d whenever wavelength is varied.

On the other hand, stray light is generally present on the diffraction grating due to imperfections in the grating itself or irregular reflection at its surface. This stray light has a greater influence in the plane consisting of the dispersion direction perpendicular to the grooves than in the direction parallel to the grooves. If either one of the light rays $L_S$ and $L_R$ is extremely weak, the stray light of the stronger light passes through the exit pin-holes for the weaker light and causes measurement error.

If the light possesses a continuous spectrum, and further, the exit pin-holes d and c lie in a plane consisting of the dispersion direction, then light having spectrum components other than the object spectrum component for measurement passes mutually through other exit pin-holes whereby accurate measurement becomes impossible.

SUMMARY OF THE INVENTION

It is therefore the primary object of the present invention to provide a method of removing measurement error arising from the fluctuation in the intensity of the incident light, absorption and scattering by interrupting molecules, etc., by a simple mechanism using one dispersive element.

The present invention provides a spectrophotometer employing a magneto-optic effect of the type which is equipped with means for applying a magnetic field to a sample to be measured and which analyzes the sample by irradiating the sample with linearly polarized light emitting a spectrum which includes a resonance line of the sample, separating the incident light into two light rays having polarization components perpendicular to each other, converging these two light rays having polarization components perpendicular to each other, spectrally analyzing the two light rays using a dispersive element and detecting the resulting two light beams by a double beam method to thereby analyze the sample, said spectrophotometer being characterized in that the plane including the two light beams entering the dispersive element is arranged to be substantially perpendicular to the plane defined by the dispersion direction of the dispersive element.

Reference will now be had to FIG. 5 for an explanation of an example of the spectrophotometer employing the magneto-optic effect and which uses a concave diffraction grating as the dispersive element. More specifically, two light beams $L_S$, $L_R$ having the same wavelength but different polarizations are arranged such that their optical axes are present in the plane which is parallel to the direction of the grooves of the concave diffraction grating 9.

Entrance pin-holes a and b are bored through the entrance plate 7 in parallel with the direction of the grooves of the diffraction grating 9, and the beams $L_S$, $L_R$ are allowed to enter through these pin-holes. The light that has been diffracted by the diffraction grating 9 forms the images of the pin-holes a and b at positions specified by the wavelength. If the incident light is light of a single wavelength, the images become dots which are images on the exit pin-holes d and c of the exit plate 8 in FIG. 5. In this case, the surface of the concave diffraction grating 9 and the pin-holes a, b, c and d are naturally located on a Rowland's circle.

With respect to the direction of the grooves, the diffraction grating is a mere mirror which simply causes a specular reflection. Hence, the pin-holes d and c lie in a plane which is parallel to the direction of the grooves. The distance D between a line connecting the pin-holes a and b and a line connecting the pin-holes c and d varies in accordance with the wavelength of the incident light. However, the distance between c and d does not vary. When the wavelength of the incident light is varied, it is possible to form the images of the pin-holes a and b on the pin-holes d and c by turning the diffraction grating 9 around a Z-axis which is parallel to the grooves while leaving the position of the pin-holes c and d unchanged. This is exactly similar to a case in which an apparatus uses a plane diffraction grating or a prism.

DESCRIPTION OF THE PREFERRED EMBODIMENT

Embodiment

Figure 6:
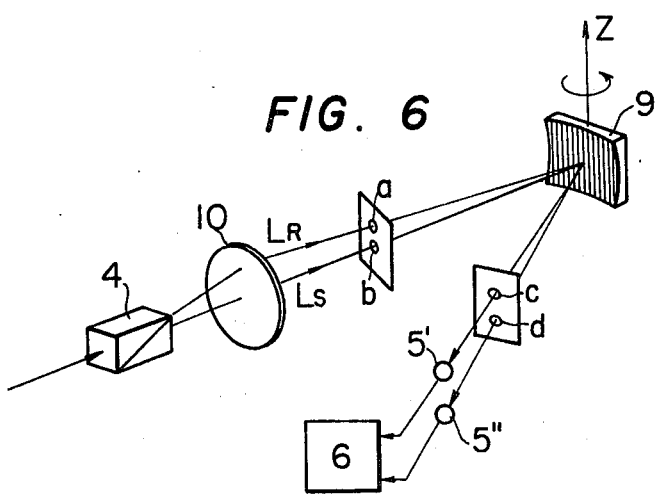
FIG. 6 is a schematic view showing the principal construction of the apparatus in accordance with an embodiment of the invention.

FIG. 6 illustrates a portion of the apparatus ranging from the analyzer to the detectors. The light ray that has passed through the sample for measurement passes through the analyzer 4 of the double image polarization prism, is separated into to beams of light $L_R$ and $L_S$ that are converged by the lens 10, pass through the entrance pin-holes a, b of the spectrometer, are diffracted by the diffraction grating 9, pass through the respective exit pin-holes d, c and then are detected by the detectors 5" and 5'. The outputs of these detectors are proportioned by the operational apparatus 6 to thereby determine the measurement output. This proportioning operation enables the compensation of measurement error resulting from the absorption and scattering by molecules, etc., with the exception of errors due to atomic vapor.

The two light beams passed through the double image polarization prism comprising the analyzer 4, the line connecting the pin-holes a and b as well as the line connecting the pin-holes c and d all lie in planes respectively which are in parallel to the grooves of the diffraction grating 9. In order to detect a different element, the wavelength must be varied. Selection of the wavelength in this instance can be made either by turning the diffraction grating 9 around the Z axis which is parallel to the grooves of the same, or by moving the set of the exit pin-holes c and d while keeping the diffraction grating 9 fixed. In other words, the wavelength can be selected by turning the diffraction grating or by a parallel translation of the set of the exit pin-holes c and d as a whole. It is not necessary to individually and separately move the pin-holes c and d.

It will now be assumed that, of the two beams of light, the beam $L_R$ is one which passes through the analyzer 4 even when the sample is not present. If the concentration of the sample is small, the other beam $L_S$ is extremely weak. If the arrangement shown in FIG. 4 is used, therefore, the stray light of $L_R$ becomes great as mentioned in the foregoing paragraph so that accurate measurement of the intensity of $L_S$ is not feasible. In accordance with the arrangement of the present invention, however, it is possible to minimize the stray light and to measure $L_S$ with a high level of accuracy. In this manner, it is possible in accordance with the present invention to measure a sample in a highly accurate manner with a double beam system of the same wavelength by the use of a simple mechanism.

Figure 7:
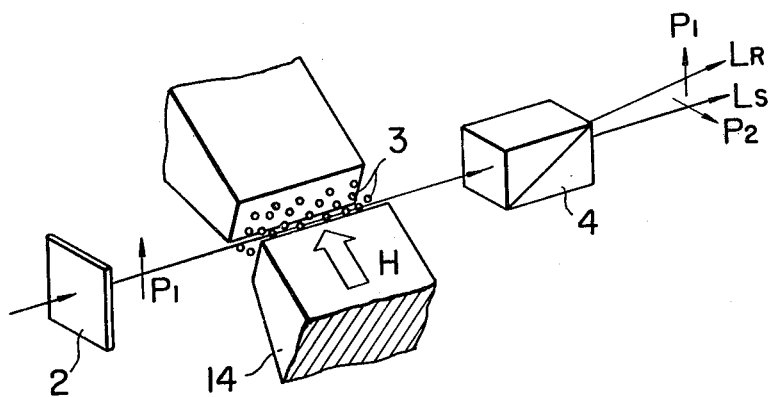
FIG. 7 is a schematic view showing a sample-accommodating section which is one of the principal sections of the apparatus in accordance with the invention.

FIG. 7 illustrates the manner in which a magnetic field is applied to the atomic vapor of the sample, and shows the disposition of the double image polarization prism. As already shown in FIGS. 1 and 3, the magnetic field is applied to the atomic vapor 3 in a direction parallel, or perpendicular to, the travelling direction of the incident light. When the magnetic field H is perpendicularly applied by the magnet 14, however, the direction coincides with the birefringence direction of a uniaxially anisotropic medium having the direction of the magnetic field H as its optic axis. In such a case, it is most desirable to arrange the direction of the magnetic field H at an angle of 45° relative to the polarization direction $P_1$ of the incident light.

The beams of light $L_R$ and $L_S$ that are separated by the analyzer 4 of the double image polarization prism and are oriented in the direction of polarization $P_1$ and the direction of polarization $P_2$ perpendicular to $P_1$, respectively, further enter the spectrometer as shown in FIG. 5. As already mentioned, the plane including the beams $L_R$, $L_S$ is perpendicular to the plane consisting of the dispersion direction of the dispersive element of the spectrometer. In producing a spectrophotometer, the plane consisting of the dispersion direction mentioned above is conveniently located in the horizontal or vertical plane so as to facilitate designing and maintenance of the apparatus. For this reason, the plane including the beams $L_R$, $L_S$ is located in the vertical or horizontal plane. Since the analyzer 4 is positioned perpendicular to the polarizer 2, the magnetic field H must be applied at an angle of 45° with respect to the horizontal plane.

Figure 8:
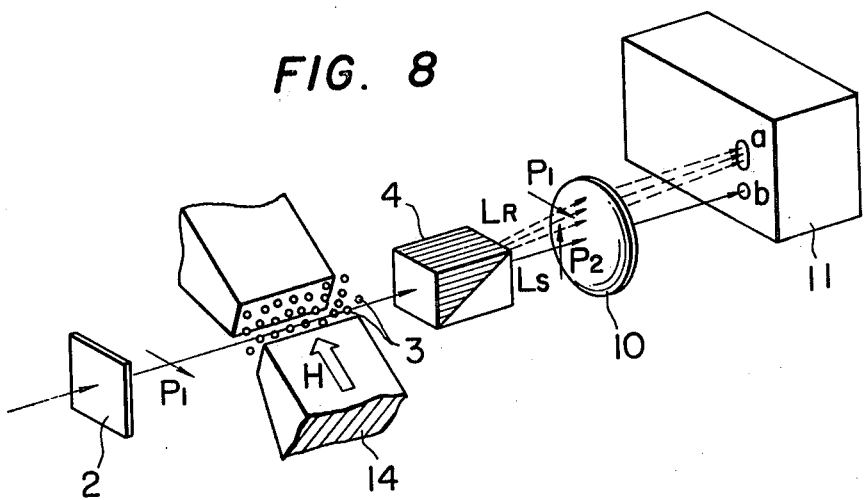
FIG. 8 is a schematic view showing a sample-accommodating section and an analyzer section of the apparatus in accordance with another embodiment of the invention.

FIG. 8 illustrates an example of the apparatus using a Rochon prism as the double image polarization prism. The analyzer 4 is arranged such that when no atomic vapor 3 is present, the incident linearly polarized light is refracted and allowed to pass through the analyzer 4 of the Rochon prism. The angle of refraction varies depending upon the wavelength and consequently, the transmitted light $L_R$ advances in varying directions in accordance with the wavelength of the incident light. When the atomic vapor 3 is present, there is formed a light component having the polarized light $P_2$ perpendicular to $P_1$ that passes through the analyzer 4 without causing refraction. Hence, the direction of this transmitted light $L_S$ is constant irrespective of the wavelength of the incident light.

These transmitted light rays $L_R$ and $L_S$ are projected into the entrance slits a and b of a spectrometer 11 by a suitable optical system placed at the back of the Rochon prism (for example, the lens 10) whereby the light having the wavelength component corresponding to the atomic resonance line of the sample to be analyzed is spectrally analyzed, taken out and detected.

Atomic resonance lines of heavy metal elements that adversely affect living creatures by contributing to environmental pollution, etc., are mostly composed of invisible ultraviolet rays. If the polarizer 2 and the analyzer 4 are disposed so as to convert, into a signal light, the light having a polarized component refracted by the analyzer 4, the optical path to the photodetectors will be varied in accordance with the wavelength due to this refraction of the light during its passage through the analyzer 4. Hence, adjustment of the optical system becomes extremely time consuming since adjustment at the initial stage is generally done using visible rays which have a different optical path than the ultraviolet rays actually used for the measurement.

If light which does not cause refraction is used as the signal light such as shown in FIG. 8, the focal distance of the lens varies depending upon wavelength. Thus, though the mode of focusing of the light beams and the like also vary in accordance with the wavelength, the position of the optical path itself does not vary. It is therefore easy to make an adjustment. Since the intensity of the reference light is great, it is relatively easy to perform the adjustment for the optical system of the reference light. It is also possible to examine the position of the optical path by converting the light into visible rays using a fluorescent material. Due to the high intensity of the reference light, it is possible to consistently cause a predetermined quantity of the reference light to reach the photodetectors by the use of only a part of the same, even when the optical path fluctuates in accordance with wavelength. In this embodiment, the same effect can be similarly obtained by the use of a Senarmont prism as the analyzer in place of the Rochon prism.

In the foregoing description, two separate pin-holes are provided for the two beams of light $L_S$, $L_R$. Since the optical path of $L_R$ differs with wavelength, however, it is sometimes more convenient to use a single common pin-hole or slit for both beams $L_S$, $L_R$. In the present invention, the two beams of light are not necessarily caused to enter the same portion of the same dispersive element, but may be allowed to enter different portions of the element.

The present invention can be adapted to a spectrophotometer employing a magneto-optic effect having another optical system. For example, the present invention can be adapted to the signal detection section of "SPECTROMETER EMPLOYING MAGNETO-OPTIC EFFECT" of Japanese Patent Application No. 30103/1975 filed by the inventors of the present invention.

As can be clearly appreciated from the foregoing description, the arrangement in the present invention ensures the detection of signals of varying wavelengths while fixing the distance between the two detectors. It is obvious in this connection that the detectors need not always be perfectly vertical, but may be deviated from each other in the vertical direction within the range which permits the measurement, provided that the distance therebetween is kept unchanged.

As described above, it is possible in accordance with the present invention to measure an optional element at a high level of accuracy by a double beam method of the same wavelength using a single dispersive element in a measuring apparatus which is easily adjustable.

What is claimed is:

1. In a spectrophotometer employing a magneto-optic effect which includes;
    a space for accommodating a sample to be measured;
    means for applying a magnetic field to said space;
    light irradiation means for irradiating said space with linearly polarized light;
    polarization-separation means for allowing entry of the light from said light irradiation means after having passed through said space, and for separating and projecting this incident light in two light beams in proportion to the intensity of two mutually perpendicular polarization components;
    spectral analyzer means equipped with means for converging the two light beams separated by said polarization-separation means and with a dispersive element for spectrally dispersing the two light beams thus converged; and
    light detection means for detecting the two light beams dispersed by said dispersive element;
    the improvement wherein said dispersive element is arranged in such a manner that the plane containing the two light beams incident on said dispersive element is substantially perpendicular to the plane defined by the dispersion direction of said dispersive element.

2. The spectrophotometer employing a magneto-optic effect as defined in claim 1, wherein the direction of application of a magnetic field by said application means is perpendicular to the direction of the incident light irradiated from said light irradiation means into said space, and defines an angle of 45° relative to the direction of polarization of the light from said light irradiation means and an angle of 45° relative to the horizontal plane.

3. The spectrophotometer employing a magneto-optic effect as defined in claim 1, wherein said light irradiation means and said polarization-separation means are arranged in such a manner that the plane including the two light beams projected from said polarization-separation means is a vertical plane.

4. The spectrophotometer employing a magneto-optic effect as defined in claim 1, wherein said polarization-separation means does not cause refraction but allows rectilinear propagation of the light entering said polarization-separation means through said space which has a direction of polarization perpendicular to that of the light irradiated from said light irradiation means.

5. The spectrophotometer employing a magneto-optic effect as defined in claim 2, wherein said light irradiation means and said polarization-separation means are arranged in such a manner that the plane including the two light beams projected from said polarization-separation means is a vertical plane.

6. The spectrophotometer employing a magneto-optic effect as defined in claim 3, wherein said polarization-separation means does not cause refraction but allows rectilinear propagation of the light entering said polarization-separation means through said space which has a direction of polarization perpendicular to that of the light irradiated from said light irradiation means.

* * * * *